US006610878B1

(12) United States Patent
Hubbs et al.

(10) Patent No.: US 6,610,878 B1
(45) Date of Patent: Aug. 26, 2003

(54) POLY(3-CYCLOPROPYL-3-HYDROXYPROPIONATE) AND PROCESSES FOR ITS PREPARATION AND DERIVATIVES THEREOF

(75) Inventors: John Clark Hubbs, Kingsport, TN (US); Theresa Sims Barnette, Rogersville, TN (US); Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/546,817

(22) Filed: Apr. 11, 2000

Related U.S. Application Data

(60) Provisional application No. 60/133,686, filed on May 10, 1999.

(51) Int. Cl.[7] .................................................. C07C 9/74
(52) U.S. Cl. ...................................................... 560/124
(58) Field of Search .......................................... 560/124

(56) References Cited

U.S. PATENT DOCUMENTS

| 3,770,781 A | 11/1973 | Rollmann et al. |
| 3,932,469 A | 1/1976 | Berg et al. |
| 3,996,248 A | 12/1976 | Wall et al. |
| 4,275,238 A | 6/1981 | Petree et al. |
| 4,296,243 A | 10/1981 | Sato |
| 4,897,498 A | 1/1990 | Monnier et al. |
| 4,950,773 A | 8/1990 | Monnier et al. |
| 5,041,613 A | 8/1991 | McCombs |
| 5,082,956 A | 1/1992 | Monnier et al. |
| 5,254,701 A | 10/1993 | Falling et al. |

FOREIGN PATENT DOCUMENTS

| EP | 847974 A1 | 6/1998 |
| EP | 0847974 | * 6/1998 |
| JP | 11035520 | 9/1999 |
| WO | WO 99/06341 | 2/1999 |

OTHER PUBLICATIONS

S. Slobodin, Zh. Obshch. Khim., 22, 1952, 243–47.
Wilson, J. Amer. Chem. Soc., 69, 3002–06 (1947).
J. E. Baldwin et al, J. Org. Chem., 1995, 60, 186–90.

* cited by examiner

*Primary Examiner*—Paul J. Killos
(74) *Attorney, Agent, or Firm*—Michael J. Blake

(57) ABSTRACT

Poly(3-cyclopropyl-3-hydroxypropionates) (I) which are useful for the preparation of vinylcyclopropane and cyclopropylacetylene are disclosed. Methods for the preparation of a variety of intermediates obtained from (I) such as 3-cyclopropyl-3-hydroxypropionic acid and esters and salts thereof, 3-cyclopropylacrylic acid, and vinylcyclopropane also are disclosed.

8 Claims, No Drawings

POLY(3-CYCLOPROPYL-3-HYDROXYPROPIONATE) AND PROCESSES FOR ITS PREPARATION AND DERIVATIVES THEREOF

This application claims benefit of provisional application Ser. No. 60/133,686 filed May 10, 1999.

INTRODUCTION

This invention pertains to poly(3-cyclopropyl-3-hydroxypropionate) compositions (I), a process for the preparation thereof and processes for the preparation of derivatives of (I). More specifically, this invention pertains to poly(3-cyclopropyl-3-hydroxypropionate) and its preparation by the reaction of cyclopropanecarboxaldehyde (CPCA) with ketene. The present invention also includes additional embodiments comprising the preparation of 3-cyclopropyl-3-hydroxypropionic acid (II) and salts (III) and esters (IV) thereof, 3-cyclopropylacrylic acid (V) and esters thereof (VI), and vinylcyclopropane (VII) from poly (3-cyclopropyl-3-hydroxypropionate) (I). Further embodiments of the present invention comprise a plurality of steps wherein (I) is first prepared and then converted to one or more of compounds (II), (III), (IV), (V), (VI) and (VII).

BACKGROUND OF THE INVENTION

Cyclopropylacetylene is a useful intermediate in the synthesis of reverse transcriptase inhibitors. Known processes for the synthesis of cyclopropylacetylene are limited, require the use of expensive starting materials and are difficult and expensive to practice. For example, J. M. Fortunak, Z. Wang and Y. Jin disclose in PCT Published Patent Application WO 99/06341 the condensation of cyclopropanecarboxaldehyde with malonic acid, halogenation of the formed 3-cyclopropylacrylic acid and dehydrohalogenation of the formed 1-halo-2-cyclopropylethylene to produce cyclopropylacetylene. Malonic acid is expensive and a significant weight portion of it is lost in the production of carbon dioxide byproduct. M. Nakazawa, T. Mitani, Y. Satake, S. Ohzono, G. Asanyma, and M. Shiono disclose in Published European Patent Application EP 847974 A1 a process for the halogenation of 3-cyclopropylacrylic acid followed by base treatment of the formed 2,3-dibromo-3-cyclopropylpropionic acid to produce cyclopropylacetylene. S. Slobodin, Zh. Obshch. Khim., 22, 1952, 195, 197, discloses the treatment of vinylcyclopropane with bromine and treatment of the formed (1,2-dibromoethyl)cyclopropane with potassium hydroxide in 2-ethoxyethanol to inherently produce the unisolated intermediates 1-bromo-1-cyclopropylethylene and 1-bromo-2-cyclopropylethylene which are converted under the basic reaction conditions to cyclopropylacetylene. Vinylcyclopropane is difficult to prepare and is not commercially available in bulk.

In view of the above-described state of the art, it would be very desirable to produce vinylcyclopropane and 3-cyclopropylacrylic acid using inexpensive and readily available starting materials.

BRIEF SUMMARY OF THE INVENTION

The first embodiment of the present invention concerns novel poly(3-cyclopropyl-3-hydroxypropionate) compositions (I) and the preparation thereof, i.e., compositions (I) having the general formula:

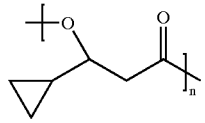

wherein n is an integer greater than 1, e.g., 2 to 2000, preferably 10 to 500, and most preferably, about 10 to 100. Compositions (I) may be prepared by contacting cyclopropanecarboxaldehyde (CPCA) and ketene in the presence of a catalyst.

Further embodiments of our invention include:
(a) The preparation of 3-cyclopropyl-3-hydroxypropionic acid (II) by contacting (I) with water.
(b) The preparation of metal 3-cyclopropyl-3-hydroxypropionate salts (III) by contacting (I) with an aqueous metal base.
(c) The preparation of alkyl 3-cyclopropyl-3-hydroxypropionate esters (IV) and the oxidation products thereof by contacting (I) with an alkanol.
(d) The preparation of 3-cyclopropylacrylic acid (V) by heating (I).
(e) The preparation of alkyl 3-cyclopropylacrylate esters (VI).
(f) The preparation of vinylcyclopropane (VII) by heating (I).
(g) The preparation of a mixture of 3-cyclopropylacrylic acid (V) and vinylcyclopropane (VII) by heating (I).
(h) The preparation of vinylcyclopropane (VII) by heating 3-cyclopropyl-acrylic acid (V)
(i) The preparation of vinylcyclopropane (VII) by heating 3-cyclopropyl-3-hydroxypropionic acid (II)
(j) 3-Cyclopropyl-3-acyloxypropionic acids wherein the acyloxy group is the residue of a $C_2$–$C_{14}$ carboxylic acid (VIII).
(k) The preparation of vinylcyclopropane (VII) by the steps comprising:
(1) contacting 3-cyclopropyl-3-hydroxypropionic acid (II) with a carboxylic acid anhydride to provide an anhydride of a 3-cyclopropyl-3-acyloxy-propionic acid (VIII); (2) contacting the anhydride from step (1) with water to form a 3-cyclopropyl-3-acyloxypropionic acid (VIII); and (3) contacting the 3-cyclopropyl-3-acyloxypropionic acid from step (2) with heat, an acid or a base to convert acid (VIII) to vinylcyclopropane (VII).
(l) A mixed carboxylic anhydride comprising a 3-cyclopropyl-3-acyloxy-propionyl residue and the acyl residue of a carboxylic acid.
(m) The preparation of 3-cyclopropyl-3-hydroxypropionic acid (II) by contacting 3-cyclopropylacrylic acid (V) with water.
(n) 3-Cyclopropyl-beta-propiolactone.
(o) The preparation of vinylcyclopropane by heating 3-cyclopropyl-betapropiolactone.

Further embodiments of the invention include the combination of the step of preparing composition (I) with any of processes (b), (d), and (f)–(i). The compositions which may be obtained in accordance with the present invention may be converted ultimately to cyclopropylacetylene according to known procedures such as those discussed hereinabove.

DETAILED DESCRIPTION OF THE INVENTION

As mentioned above, the first embodiment of the present invention concerns novel poly(3-cyclopropyl-3- hydroxypropionate) compositions (I) and the preparation thereof. The novel compositions (I) have the general formula:

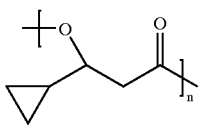

wherein n is an integer greater than 1, e.g., 2 to 2000, preferably 10 to 500, and most preferably, about 10 to 100. Because of their lower viscosity and ease of handling, compositions (I) having lower molecular weights, e.g., wherein n is an integer of 10 to 500 are preferred. The most preferred compositions (I) are those wherein n is an integer of 10 to 100. As used herein n when multiplied by the molecular weight of the repeat unit in the polymer defines the number average molecular weight for the polymer.

The novel poly(3-cyclopropyl-3-hydroxypropionates) may be prepared by the reaction of ketene and CPCA in the presence of a catalyst and, optionally, in the presence of solvent. Catalysts for the reaction include Lewis acids, e.g., salts such as halides, carboxylates and alkoxides of various metals such as alkali metals, alkaline earth metals, and transition metals, e.g., lithium, sodium, potassium, rubidium, cesium, beryllium, magnesium, calcium, strontium, barium, manganese, osmium, titanium, aluminum, zinc, cadmium, mercury, copper, silver, gold, nickel, palladium, platinum, cobalt, rhodium, iridium, iron, ruthenium, chromium, molybdenum, tungsten, vanadium, niobium, tantalum, zirconium and hafnium, tin, lead and antimony; boron trifluoride; and tertiary amines such as trialkylamines, e.g., trialkylamines containing a total of up to about 30 carbon atoms, pyridine, N-alkylmorpholine and the like. The anion of the salts may be a halide, e.g., chloride or bromide; a carboxylate selected from the residues of saturated and unsaturated, branched or linear aliphatic, mono- and poly-carboxylic acids; and alkoxides containing up to about 12 carbon atoms. Zinc, iron and magnesium salts of aliphatic, mono-carboxylic acids containing 2 to 20 carbon atoms represent the preferred metal carboxylate catalysts. Specific examples of such compounds include iron acetate, magnesium acetate, zinc acetate and zinc 2-ethylhexanoate. These catalysts may be employed in concentrations of up to 10 weight percent, based on the weight of the metal or amine component of the catalyst and the weight of the final polymer (I) product. Normally, the catalyst will be used in concentrations of about 100 to 10,000 parts per million by weight (ppmw), preferably about 200 to 3000 ppmw (same basis).

Although the process for the preparation of the poly(3-cyclopropyl-3-hydroxypropionates) may be carried out over a broad temperature range, e.g., −20 to 250° C., the use of temperatures in the range of about 0 to 100° C. are more typical. The preferred reaction temperatures are in the range of about 40 to 70° C. to allow for cooling by rapid heat transfer while minimizing any decomposition of the polymer. Reaction pressure is not an important consideration and thus pressures moderately above or below ambient pressure may be used.

It is preferred that the ketene reactant be added continuously or intermittently to an excess of CPCA in order to minimize the side reaction of ketene with itself to form diketene. If desired, an inert (non-reactive) solvent may be used, for example, to reduce viscosity and/or to aid in heat transfer and in the dissipation of heat from the reaction. The optional solvent should be inert and stable to the reaction conditions and temperatures and yet solubilize ketene and CPCA. Preferred solvents include aprotic solvents such as ethers, e.g., diethylether, diethoxymethane and tetrahydrofuran; dialkyl sulfoxides, e.g., dimethylsulfoxide; N,N-dialkylformamides and N,N-dialkyl acetamides, e.g., N,N-dimethylformamide and N,N-dimethyl-acetamide; N-alkylpyrrolidinones such as N-methylpyrrolidinone; aromatic hydrocarbons containing about 6 to 12 carbon atoms such as alkyl- and dialkyl-benzenes, e.g., toluene, 1,2-, 1,3-, and 1,4-xylenes, and 1,2-, 1,3-, and 1,4-diisopropylbenzenes; and aliphatic hydrocarbons containing from 5 to 12 carbon atoms, e.g., pentane, hexane, heptane and petroleum ether. The synthesis of composition (I) is carried out under substantially anhydrous conditions.

The crude product (I) obtained from the process described above typically contains some unreacted materials which may be removed by heating under reduced pressure, e.g., pressures of less than 800 Torr, preferably about 500 to 0.1 Torr. For low temperature processing, higher vacuums, e.g., 0.1 to 10 Torr, are necessary. The purified composition (I) thus obtained may be stored or, preferably, used to prepare any of various derivatives.

The terminal or end groups of polymer (I) may be an organic residue or a residue of a catalyst. For example, when using a zinc carboxylate as the catalyst, it is believed the end groups of the polymer of formula I consist of acetoxy groups and acetyl groups.

Further embodiments of the present invention are directed to the preparation of 3-cyclopropyl-3-hydroxypropionic acid (II), metal 3-cyclo-propyl -3-hydroxypropionate salts (III), and alkyl 3-cyclopropyl-3-hydroxy-propionate esters (IV). Compound (II) may be prepared by contacting composition (I) with water in the presence of an acid catalyst, e.g., a non-oxidizing mineral acid such as a hydrogen halide, e.g., hydrogen chloride or hydrogen bromide; sulfuric acid; phosphoric acid; sulfonic acids such as alkyl- and aryl-sulfonic acids, e.g., methanesulfonic, benzenesulfonic and toluenesulfonic acids, and acidic ion exchange resins containing pendant sulfonic acid groups, e.g., styrene/divinylbenzene polymers containing residues of styrenesulfonic acid; and the like. The amount of water employed may be in the range of 0.5 to 100 parts by weight water per part by weight of composition (I) used. If desired, a water-miscible solvent such as a $C_1$ to $C_3$ alkanol, dimethylsulfoxide or tetrahydrofuran may be employed. When used, the weight ratio of the optional water-miscible solvent:water may be in the range of about 1:1 to 1:100. The amount of acid catalyst used typically will cause the aqueous phase to have a pH of less than about 7, preferably less than about 5. The hydrolysis procedure used in the synthesis of (II) may be carried out at a temperature of about −10 to 200° C., preferably at a temperature of about 60 to 110° C. (II) may be recovered from the crude hydrolysis mixture by conventional techniques, e.g., by ion exchange, distillation, extraction, or a combination of extraction and distillation.

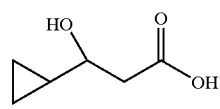

The metal 3-cyclopropyl-3-hydroxypropionate salts (III), or mixture of (III) and salts of (V), may be prepared by a saponification procedure which is substantially identical to the hydrolysis procedure described in the preceding paragraph except that a base is used at near equivalence or in molar excess. The metal ion (M) component of salts (III) may be selected from the alkali and alkaline earth metals as well as zinc, magnesium and iron. The metal ion component of (III) preferably is sodium or potassium. The preparation of (III) is carried out using conditions similar to those described above for the preparation of acid (II) except that a base is included in the procedure. The base may be selected from the hydroxides, carbonates and bicarbonates of the alkali metals, alkaline earth metals, zinc, iron, and the like. The base preferably is selected from sodium hydroxide, sodium carbonate, sodium bicarbonate, potassium hydroxide, potassium carbonate, potassium bicarbonate or a mixture of any 2 or more thereof. The amount of base used typically will be at least 1 equivalent per equivalent of 3-cyclopropyl-3-hydroxypropionate salt produced. The amount of base used normally will cause the aqueous phase to have a pH of greater than about 8.5, i.e., at the commencement of the saponification, preferably greater than about 10. Salts (III) may be converted to acid (II) by contacting the former with an acid such as hydrochloric acid, sulfuric acid or an acidic ion exchange resin according to conventional acidification procedures.

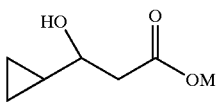

III

Alkyl 3-cyclopropyl-3-hydroxypropionate esters (IV) may be prepared by contacting composition (I) with an alcohol in the presence of an acid catalyst or base in a manner analogous to the hydrolysis and saponification procedures described in the preceding paragraphs. Examples of the alcohols which may be used are compounds having the structure $R^1OH$ wherein $R^1$ is an alkyl radical, including substituted alkyl such as aryl-substituted alkyl, containing up to about 12 carbon atoms. Preferred $R^1$ groups include methyl, ethyl, n-propyl, n-butyl, n-pentyl and benzyl. Benzyl-3-cyclopropyl-3-hydroxypropionate is a particularly preferred ester (IV) due to the ease of removal of the benzyl group by catalytic hydrogenation. The amount of alcohol $R^1OH$ employed may be in the range of 2 to 100 parts by weight alcohol per part by weight of composition (I) used. This alcoholysis procedure may be carried out at a temperature of about 0 to 140° C., preferably at a temperature in the range of about 0 to 100° C., most preferably in the range of about 25 to 80° C.

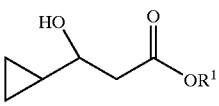

IV

When using a base, the amount of water present preferably is limited to less than 10 mole percent of the final product in order to minimize competing hydrolysis. Thus, the bases preferably are those which add no additional water to the reaction, e.g., metal alkoxides such as alkali metal alkoxides, including arylalkoxides, containing up to about 10 carbon atoms. Preferred alkali metal alkoxides are those which can be formed by addition of a zero valent alkali metal to a solution of the alcohol corresponding to the ester to be formed. Preferred alkali metal alkoxides include those derived from $C_1$–$C_{10}$ primary alcohols and alkali metals such as lithium, sodium, potassium and cesium. The sodium and potassium alkoxides of methanol, ethanol, n-propanol, n-butanol, n-pentanol, isopropyl alcohol, and benzyl alcohol represent the most preferred metal alkoxides.

The acid catalysts useful for the conversion of composition (I) to ester (IV) may be selected from hydrogen halides such as hydrochloric acid, sulfuric acid, trifluoroacetic acid, phosphoric acid and sulfonic acids such as alkyl- and aryl-sulfonic acids, e.g., methanesulfonic, benzene-sulfonic and toluenesulfonic acids, and acidic ion exchange resins containing pendant sulfonic acid groups, e.g., styrene/divinylbenzene polymers containing residues of styrene-sulfonic acid. Preferred acid catalysts are sulfuric acid and hydrogen chloride. Ester (IV) may be recovered by phase separation or by ion exchange, for example, using polymer-bound tetralkylammonium hydroxide. Esters (IV) may be converted by basic or acidic hydrolysis to 3-cyclopropy-3-hydroxypropionic acid (II) by the hydrolysis or saponification procedures described hereinabove. Because of the higher solubility of composition (I) in the alcohols used in the alcoholysis process for the preparation of (IV), lower reaction temperatures may be used in the preparation of acid (II) via ester (IV) as compared to the direct acid-catalyzed hydrolysis of (I) to (II).

Yet another embodiment of the present invention pertains to the thermal treatment, optionally in the presence of an acidic catalyst or a base and optionally in the presence of solvent, of composition (I) to produce 3-cyclopropylacrylic acid (V) as a mixture of cis- and trans-isomers (Va and Vb). This embodiment includes the co-production, and thus the preparation, of vinylcyclopropane (VII). It may be possible to control the relative amounts of 3-cyclopropylacrylic acid (V) and vinylcyclopropane (VII) which are produced from composition (I) by varying the type and amount of catalyst present in (I) and by varying the thermal, acid or base processing conditions.

Va

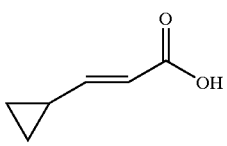

Vb

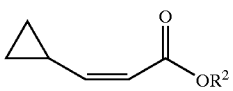

VIa

VIb

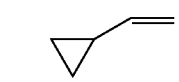

VII

It is generally preferred that no solvent be used in the preparation of vinylcyclopropane from (I). Optional solvents which may be used to produce (V) and (VII) from (I) include higher boiling solvents such as water, $C_2$ to $C_{22}$ alcohols, ethers and hydrocarbons. Optionally lower boiling solvents such as methanol may be used at higher pressures, e.g. between 1 and 1000 atmospheres of pressure ($10^5$–$10^7$ pascal). When alcohols are used under dehydrating conditions or substantially anhydrous conditions, e.g. in the presence of molecular sieves or through the formation of water azeotropes, in addition to (V) and (VII) there may also be formed esters of (V) (VI). Preferred esters are those which contain a $C_1$ to $C_{22}$ alkyl radical including substituted alkyl such as arylalkyl radicals ($R^2$). Preferred alkyl radicals include methyl, ethyl, n-propyl, n-butyl, n-pentyl and benzyl.

When aqueous bases are used for the production of 3-cyclopropyl-acrylic acid (V) from the polymer (I), it is necessary to neutralize the initially formed salt with an acid. The preferred bases for the production of salts of 3-cyclopropylacrylic acid (V) are alkali metal hydroxides. The most preferred base for the formation of sodium 3-cyclopropylacrylate is sodium hydroxide. It is preferred that the feed concentration of caustic used in the generation of sodium cyclopropylacrylate be high, preferably at least 25 weight percent of caustic in the feed. For the in situ production of trans-3-cyclopropylacrylic acid by acid neutralization of salts of 3-cyclopropyl acrylic acid, it is preferred that concentrated alkaline solutions containing the salts of 3-cyclopropylacrylic acid be neutralized with a concentrated aqueous acid, preferably hydrochloric acid, at a concentration of greater than 10 weight percent. The use of concentrated aqueous solutions at high salt strength is believed to facilitate precipitation of trans-3-cyclopropylacrylic acid (Vb).

3-Cyclopropylacrylic acid (V) and vinylcyclopropane (VII) may be obtained by heating poly(3-cyclopropyl-3-hydroxypropionates) (I) at temperatures in the range of about 75 to 300° C., preferably at temperatures in the range of about 125 to 270° C., most preferably at temperatures in the range of about 160 to 250° C. Generally, the lower temperature is chosen to permit facile reaction and the higher temperature is chosen to avoid the exothermic decomposition region for 3-cyclopropylacrylic acid and vinylcyclopropane. The (V):(VII) product ratio produced from (I) may vary depending upon the particular catalyst and/or reaction conditions employed. The catalysts which are useful for the preparation of (V) and (VII) from I are the same as those which are useful for the preparation of (I) from ketene and CPCA.

Another means for the preparation of vinylcyclopropane (VII) comprises heating 3-cyclopropylacrylic acid (V), optionally in the presence of an acidic catalyst, e.g., a Lewis acid. The conversion of (V) to (VI) is believed to be facilitated by the acid catalyzed oligomerization of (V) to low molecular weight polymers of (I). The preferred catalysts for the oligomerization of (V) to (I) are the same as those for the preparation of (I) from ketene and CPCA. The oligomerization of (V) may be carried out at temperatures of about 100 to 300° C., preferably at temperatures in the range of about 150 to 250° C. The acid catalysts for the oligomerization of (V) to (I) may be selected from 3-cyclopropylacrylic acid, phosphoric acid, and zinc alkanoates such as zinc acetate and zinc 2-ethylhexanoate.

Another embodiment of the present invention concerns the preparation of vinylcyclopropane (VII) from 3-cyclopropyl-3-hydroxy-propionic acid (II) by the solution or gas phase pyrolysis of 3-cyclopropyl-3-hydroxypropionic acid, optionally in the presence of a catalyst. The gas phase pyrolysis may be conducted at temperatures in the range of about 100 to 400° C., preferably at temperatures in the range of about 150 to 350° C.

Another means for the preparation of vinylcyclopropane (VII) from 3-cyclopropyl-3-hydroxypropionic acid (II) comprises contacting 3-cyclo-propyl -3-hydroxypropionic acid (II) with a $C_2$–$C_{14}$ carboxylic acid anhydride to provide a mixed anhydride of 3-cyclopropyl-3-acyloxypropionic acid which optionally may be heated to form the symmetrical anhydride of 3-cyclopropyl-3-acylyoxypropionic acid. These anhydrides may be reacted with water under mild conditions to produce a 3-cyclopropyl-3-acyloxy-propionic acid (VIII) wherein the acyloxy group is the residue of a $C_2$–$C_{14}$ carboxylic acid. Preferred acyloxy residues include those derived from acetic acid, propionic acid, benzoic acid, 3-cyclopropylacrylic acid and 3-cyclopropyl -3-acetoxypropionic acid. Upon treatment with acid, base or heat, 3-cyclopropyl-3-acyloxypropionic acid (VIII) readily loses carbon dioxide and a $C_2$–$C_{14}$ acid or its salt to form vinylcyclopropane (VII).

VIII

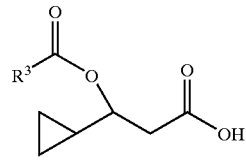

In a preferred process for the preparation of vinylcyclopropane (VII) from 3-cyclopropyl-3-hydroxypropionic acid (II), (II) is first treated with acetic anhydride to provide the mixed acetyl/3-cyclopropyl-3-acetoxypropionyl anhydride which optionally may be heated to form the symmetrical anhydride of 3-cyclopropyl-3-acetoxypropionic acid. These anhydrides are reacted with water under mild conditions to provide 3-cyclopropyl-3-acetoxypropionic acid. Upon treatment with acid, base, heat or a combination thereof, 3-cyclopropyl-3-acetoxypropionic acid is converted to vinylcyclopropane (VII) upon the liberation of carbon dioxide and acetic acid or its salts from the 3-cyclopropyl-3-acetoxypropionic acid.

Another embodiment of the present invention provides a process for the production and/or coproduction of 3-cyclopropyl-β-propiolactone of formula (IX) in the presence of certain acid catalysts, ketene and cyclopropanecarboxaldehyde. The more preferred catalysts for the production and coproduction of (IX) are believed to include boron trifluoride etherate. The 3-cyclopropyl-beta propiolactone of formula (IX) may be thermally treated, optionally in the presence of acid or base catalysts to produce vinylcyclopropane (VII).

IX

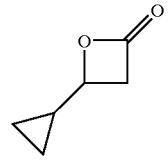

An alternate process for the preparation of 3-cyclopropyl-3-hydroxy-propionic acid (II) comprises contacting cis- or trans-3-cyclopropylacrylic acid (Va or Vb) or mixtures thereof with water under acidic or basic conditions to produce a mixture of trans-3-cyclopropylacrylic acid and 3-cyclopropyl-3-hydroxypropionic acid or salts thereof. The trans-3-cyclopropylacrylic acid produced may contain small amounts of the cis-isomer depending upon the conditions employed in its production and isolation. This embodiment of our invention may be performed at temperatures in the range of about 0 to 150° C., preferably at a temperature in the range of about 60 to 110° C., in the presence of water. Water miscible solvents such as $C_1$ to $C_3$ alkanols, dimethylsulfoxide and tetrahydrofuran can be used in conjunction with water. The acidic catalysts useful in this embodiment include those which are miscible with water, e.g., hydrogen halides such as hydrogen chloride, sulfuric acid and phosphoric acid. Similarly, the basic catalysts and reagents are those which are soluble in or miscible with water, e.g., the hydroxides, carbonates and bicarbonates of the alkali metals and alkaline earth metals. Sodium hydroxide, sodium carbonate, sodium bicarbonate, potassium hydroxide, potassium carbonate, and potassium bicarbonate are especially preferred basic catalysts.

In the preparation of 3-cyclopropyl-3-hydroxypropionic acid (II) from cis- or trans-3-cyclopropylacrylic acid (Va and Vb), the ratio of 3-cyclo-propyl-3-hydroxypropionic acid to 3-cyclopropylacrylic acid may be increased by use of increasing amounts of water. The ratio of trans-3-cyclopropylacrylic acid to 3-cyclopropyl-3-hydroxypropionic acid may be increased by the use of concentrated aqueous solutions or in mixed aqueous-organic organic solvents wherein the water is maintained at less than 50 weight percent and the organic solvent is chosen from water-miscible, aprotic solvents. For increased ratios of trans-3-cyclopropylacrylic to 3-cyclopropyl-3-hydroxypropionic acid, the preferred concentration of the water component is less than 25 weight percent and even more preferred is less than 10 weight percent, e.g., from about 100 ppmw to 5 weight percent. The preferred aprotic solvents include tetrahydrofuran, N,N-di-methylformamide, 1,2-dimethoxyethane, dimethoxymethane, diethoxy-methane and dimethylsulfoxide. For those solvent compositions and concentrations which favor the production of trans-3-cyclopropylacrylic acid, this process constitutes a method for the isomerization of cis-3-cyclopropyl-acrylic acid into trans-3-cyclopropyl-acrylic acid. For those solvent compositions of relatively low water concentration which favor the interconversion or production of cyclopropylacrylic acid or its salts from 3-cyclopropyl-3-hydroxypropionic acid or its salts, this process constitutes a method for the production of cyclopropylacrylic acid or its salts from 3-cyclo-propyl-3-hydroxypropionic acid When protic water miscible solvents such as $C_1$ to $C_3$ alkanols are used for the preparation of 3-cyclopropyl-3-hydroxypropionic acid (II) from cyclopropylacrylic acid (V), there may also be formed ethers, e.g., alkyl 3-cyclopropyl-3-alkoxypropionate esters (X). The formation of alkyl 3-cyclopropyl-3-alkoxypropionate esters (X) may be favored by the use of high concentrations of alcohol ($R^4OH$) in the relative or complete absence of water. The catalysts and temperatures useful for the formation of alkyl 3-cyclopropyl-3-alkoxypropionate esters (X) are the acid catalysts which are useful in the preparation of 3-cyclopropyl-3-hydroxypropionic acid (II) from cyclopropylacrylic acid (V). Preferred alkyl 3-cyclopropyl-3-alkoxypropionate esters (X) are methyl 3-cyclopropyl-3-methoxypropionate, ethyl 3-cyclo-propyl-3-ethoxypropionate, and n-propyl 3-cyclopropyl-3-n-propoxypropionate The alkyl 3-cyclopropyl-3-alkoxypropionate esters (X) may be hydrolyzed to the 3-cyclopropyl-3-alkoxypropionic acids which may be thermally treated to produce vinylcyclopropane (VII).

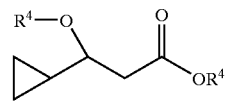

X

A further embodiment of the present invention pertains to the conversion of 3-cyclopropyl-3-hydroxypropionic acid (II), metal 3-cyclo-propyl-3-hydroxypropionate salts (III), and alkyl 3-cyclopropyl-3-hydroxy propionate esters (IV) to alkyl esters of 3-cyclopropyl-3-oxopropionic acid or methylcyclopropylketone (MCPK) by oxidation of the 3-hydroxy group to a 3-keto-functionality. The 3-cyclopropyl-3-hydroxypropionic acid (II), metal 3-cyclopropyl-3-hydroxypropionate salts (III), and alkyl 3-cyclopropyl-3-hydroxypropionate esters (IV) used in the preparation of MCPK preferably are prepared from poly(3-cyclopropyl-3-hydroxypropionates) (I). Oxidation of the 3-cyclopropyl-3-hydroxypropionic acid (II) produces 3-keto-3-cyclopropylpropionic acid, also known as 3-cyclopropyl-3-oxopropionic acid. Typically, 3-keto-3-cyclopropylpropionic acid is an unisolated intermediate that readily looses carbon dioxide at temperatures between 0 and 300° C. to produce MCPK. Preferred temperatures for the decarboxylation of 3-keto-3-cyclopropylpropionic acid are between 25 and 150° C. Oxidation of the metal 3-cyclopropyl-3-hydroxypropionate salts (III) produces 3-keto-3-cyclopropylpropionic acid salts which upon acidification provide the typically unisolated 3-cyclopropylpropionic acid. Alternatively, the 3-keto-3-cyclopropylpropionic acid salts may be directly decarboxylated to MCPK by subjecting the 3-keto-3-cyclopropylpropionic acid salts to temperatures between 0 and 300° C. in the presence of a protic solvent, preferred protic solvents being $C_1$–$C_6$ alcohols and water. Preferred temperatures for the decarboxylation of 3-keto-3-cyclopropylpropionic acid salts are between 100 and 200° C. Preferred metal ions for the metal salts of 3-keto-3-cyclopropylpropionic acid salts are the same as the preferred metal ions for metal 3-cyclopropyl-3-hydroxypropionate salt s (III). Oxidation of the alkyl 3-cyclopropyl-3-hydroxypropionate esters (IV) provides alkyl 3-keto-3-cyclopropylpropionate which may be hydrolyzed by acid or basic aqueous hydrolysis conditions to provide the MCPK intermediates 3-keto-3-cyclopropylpropionic acid salts and 3-keto-3-cyclopropylpropionic acid.

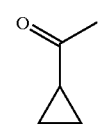

MCPK

The 3-cyclopropyl-3-hydroxypropionic acid (II), metal 3-cyclopropyl-3-hydroxypropionate salts (III), and alkyl 3-cyclopropyl-3-hydroxypropionate esters (IV) may be oxidized to the ketones, MCPK, alkyl 3-cyclopropyl-3-oxopropionates, 3-keto-3-cyclopropylpropionic acid, 3-keto-3 -cyclo-propylpropionic acid salts or mixtures thereof upon treatment with oxidizing agents, optionally in the presence of a solvent and optionally in the presence of an added hydrogen acceptor, e.g. an added ketone or olefin, oxygen, hydrogen peroxide, peracids or a combination thereof. The most preferred alkyl 3-cyclopropyl-3-oxopropionate is methyl 3-cylopropyl-3-oxopropionate (MCOP). Preferred conditions for the oxidation included the use of periodates or transition metal catalysts optionally in the presence of hydrogen acceptors, e.g., molecular oxygen. Preferred transition metal catalysts contain zero valent or oxidized states, e.g. up to an oxidation state of seven, of transition metals chosen from aluminum, manganese, osmium, titanium, zinc, cadmium, mercury, copper, silver, gold, nickel, palladium, platinum, cobalt, rhodium, iridium, iron, ruthenium, chromium, molybdenum, tungsten, vanadium, niobium, tantalum, zirconium and hafnium, tin, lead and antimony. Even more preferred transition metal catalysts are chosen from osmium, nickel, palladium, platinum, silver and rhodium. Highly preferred catalysts include potassium periodate; platinum or palladium in the zero valent state; sodium hypochlorite; manganese dioxide; and especially chromium trioxide or chromic acid or its salts in an oxidation state of six. Optional solvents for the oxidation of 3-cyclopropyl-3-hydroxypropionic acid (II), metal 3-cyclopropyl-3-hydroxypropionate salts (III), and alkyl 3-cyclopropyl-3-hydroxypropionate esters (IV) include those which dissolve the substrate and are generally unreactive to the oxidizing conditions. Such solvents include water, $C_1$–$C_{22}$ aliphatic hydrocarbons, $C_1$–$C_{12}$ dialkyl ethers, aromatic hydrocarbons and halogenated hydrocarbons. Preferred solvents include water, methanol, pentane, hexane, heptane, methylene chloride, carbon tetracholoride and perchloroethylene. Preferred temperatures for the oxidation are not believed to be particularly critical and may vary between 0 and 300° C. in the solution phase and between 25 and 600° C. in the gas phase.

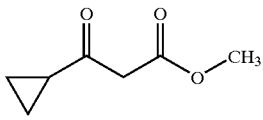

MCOP

The 3-cyclopropylacrylic acid (V) and vinylcyclopropane (VII) which may be obtained from (I) may be each individually or as a mixture treated with a halogenating agent and then a basic reagent to promote dehydro-halogenation to cyclopropylacetylene. The most preferred intermediate for conversion to cyclopropylacetylene is vinylcyclopropane due to ease of handling and simplified operating procedures. Useful halogenating agents include chlorine, bromine and iodine, preferably chlorine and bromine, and most preferably bromine. The halogenation of (V) or (VII) may be carried out in solvents which are inert or react slowly with halogenating reagents. Examples of suitable solvents include $C_1$–$C_{10}$ linear, branched, or cyclic aliphatic hydrocarbons, halogenated aliphatic hydrocarbons, haloaromatics, a $C_2$ to $C_5$ aliphatic carboxylic acid, or mixtures thereof. Preferred aliphatic hydrocarbon solvents are pentane, isopentane, hexane, cyclohexane, or heptane. Preferred halogenated solvents are carbon tetrachloride, chloroform, dichloromethane, and tetrachloroethane. Preferred haloaromatics for use as solvents are chlorobenzene, dichlorobenzene, and benzotrifluoride.

The halogenation of 3-cyclopropylacrylic acid (V) and vinylcyclopropane (VII) or mixtures thereof may be performed at a temperature of about −50 to 150° C., preferably at temperatures in the range of about 0 to 80° C. The preferred basic reagents for dehydrohalogenation of the halogenation products of 3-cyclopropylacrylic acid (V) or vinyl-cyclopropane (VI) are alkali metal hydroxides and alkali metal alkoxides, especially potassium hydroxide. The dehydrohalogentation normally is carried out in a polar aprotic solvent or a polar protic solvent. Examples of suitable polar aprotic solvents include dimethylsulfoxide, N,N-dimethyl-formamide, N-methylpyrrolidone, 1,2-dimethoxyethane, diethoxymethane, and dimethoxymethane. The most preferred polar aprotic solvent is dimethylsulfoxide. Examples of polar protic solvents include the monomeric and oligomeric addition products of a $C_1$–$C_3$ alkanol to ethylene oxide or $C_1$–$C_6$ alcohols. 2-Ethoxyethanol and 2-methoxyethanol are particularly preferred polar protic solvents. The dehydrohalogenation of the halogenation products of 3-cyclopropylacrylic acid, and vinylcyclopropane or mixtures thereof may be carried out at temperature of about −20 and 200° C., preferably at a temperature in the range of about 40 to 110° C.

The cyclopropanecarboxaldehyde (CPCA) used in the present invention may be obtained by the thermal isomerization or rearrangement of 2,3-dihydrofuran. For example, U.S. Pat. No. 4,275,238 describes passing 2,3-dihydrofuran through a column at 480° C. to obtain CPCA having a purity of 90% and containing 6.2–6.7% crotonaldehyde. A similar procedure is described by Wilson, *J. Amer. Chem. Soc.*, 69, 3002 (1947). 2,3-Dihydro-furan may be obtained according to the process described in U.S. Pat. No. 5,254,701 by the isomerization of 2,5-dihydrofuran which in turn can be produced by the isomerization of 3,4-epoxy-1-butene as described in U.S. Pat. Nos. 3,932,469, 3,996,248 and 5,082, 956. U.S. Pat. Nos. 4,897,498 and 4,950,773 describe the preparation of 3,4-epoxy-1-butene by the selective monoepoxidation of butadiene.

The novel processes and compositions provided by the present invention are further illustrated by the following examples. Proton and carbon nuclear magnetic resonance (NMR) spectra were recorded on a Varian Gemini 300 NMR instrument operating at 300 MHz in proton mode and 75 MHz in carbon mode. All NMR spectra are referenced to tetra-methylsilane (TMS) at 0 parts per million (ppm) and peak frequencies are recorded in ppm unless otherwise specified. NMR coupling constants (J) are reported in Hertz (Hz) as the distance between peak line frequencies and are uncorrected. Where NMR coupling constants are reported, the data were obtained at a measured resolution of less than 1 Hz (as measured by TMS linewidth at half height). Mass spectra (MS) were obtained using a VG Analytical Ltd. Model ZAB-1F Mass Spectrometer in EI (electron impact), fast atom bombardment (FAB, Xenon gas) or FD (field desorption) mode. Gas chromatography-mass spectroscopy (GCMS) was conducted using a VG 70-SEQ instrument equipped with a 30 meter DB5 capillary column (J and W Scientific) using helium carrier gas in electron impact mode. Gel permeation chromatography (GPC) data were acquired on a Waters Model 150C gel permeation chromatograph. The mobile phase was chloroform or tetrahydrofuran. GPC reported molecular weights are reported for only the polymer fraction and are uncorrected relative to polystyrene.

Unless otherwise specified, all reactions were carried out under an inert atmosphere of argon or nitrogen and were stirred magnetically. Cyclopropanecarboxaldehyde (CPCA) was distilled prior to use. Ketene was prepared by passing diketene through a heated tube at a temperature between 500 and 600° C. The formed gas was either condensed in a dry ice bath at −78° C. and redistilled into the reaction vessel or directly transferred into the reaction vessel.

EXAMPLE 1

Preparation of poly(3-cyclopropyl-3-hydroxypropionate) from zinc acetate (approximately 2000 ppmw Zn), ketene and CPCA.

CPCA (53.6 g, 0.77 moles) was charged to a 0.3 L, 2-neck flask with a built in thermowell. Zinc acetate dihydrate (0.47 g, 0.0021 moles, 2000 ppm Zn based on the CPCA charge) was added as a single charge and stirred until a homogenous solution was obtained. Ketene was introduced through an extra coarse fritted gas inlet tube and allowed to exit the reaction vessel through a dry ice cooled condenser. Approximately 36.5 g of ketene (0.87 moles) was added over the course of 35 minutes. The reaction temperature was maintained between 35 and 51° C. by application of an external cooling bath. Proton NMR analysis confirmed the production of poly(3-cyclopropyl-3-hydroxypropionate) in the presence of approximately 16 mole percent of unreacted cyclopropylcarboxaldehyde.

GPC (CHCl$_3$): Mp(peak molecular weight=3200; Mn (number average molecular weight)=1270; Mw (weight average molecular weight)=3490

EXAMPLE 2

Preparation of poly(3-cyclopropyl-3-hydroxypropionate) from zinc acetate (approximately 300 ppmw Zn), ketene and CPCA.

CPCA (203.3 g, 2.9 moles) was charged to a 0.5 L, 2-neck flask with a built in thermowell. Zinc acetate dihydrate (0.203 g, 0.00092 moles, 300 ppmw Zn based on the CPCA charge) was added as a single charge and stirred until a homogenous solution was obtained. Ketene was introduced through an extra coarse fritted gas inlet tube and allowed to exit the reaction vessel through a dry ice cooled condenser. Approximately 99 g of ketene (2.4 moles) was added over the course of 2.3 hours. After an initial warm-up period, the reaction temperature was maintained between 42 and 61° C. by application of an external cooling bath during the early phase of the reaction (approximately 1.5 hour) and with external heating during the latter phases of the reaction. Proton NMR analysis confirmed the production of poly(3-cyclopropyl-3-hydroxypropionate) in the presence of approximately 30 mole percent of unreacted cyclopropyl-carboxaldehyde. A small amount of diketene (approximately 8 mole %) also was detected.

$^1$H NMR (CDCl$_3$): 4.66(m, 1H); 2.68(m, 2H); 1.04(m, 1H); 0.50(m, 3H); 0.34 (m, 1H).

GPC (CHCl$_3$): Mp(peak molecular weight=11700; Mn (number average molecular weight)=3300; Mw (weight average molecular weight)=13700.

EXAMPLE 3

Hydrolysis of poly(3-cyclopropyl-3-hydroxypropionate).

Poly(3-cyclopropyl-3-hydroxypropionate) was prepared according to the procedure described in Example 2. The CPCA monomer present in the crude product was removed by vacuum treatment (1–7 Torr) and brief heating of the polymer (20 minutes) to 100° C. The thus formed poly(3-cyclopropyl-3-hydroxypropionate) (17 g) and sodium bicarbonate (25.5 g, 0.30 moles, approximately 2 equivalents relative to the calculated number of moles of polymer repeat units) were charged to a reaction vessel containing distilled water (0.1 L). The reaction mixture was vigorously refluxed until a solution was obtained (approximately 5 hours). A portion of the reaction solution (5 mL) was filtered through a resin bed containing 0.09 L of water washed cation exchange resin in the hydrogen ion form (Bio-Rad, AG 50W-X2 Resin, 100–200 mesh, 0.15 to 0.075 mm). The ion exchange resin was washed with several volumes of water and the eluate was freeze dried. Proton NMR analysis of the freeze dried product indicate the presence of 3-cyclopropyl-3-hydroxypropionic acid and trans-3-cyclo-propylacrylic acid in a molar ratio of approximately 2.5:1.

$^1$H NMR (CDCl$_3$, 3-cyclopropyl-3-hydroxypropionic acid component): 3.34 (m, 1H); 2.73(dd, 1H, J=16.2, 3.8); 2.65 (dd, 1H, 16.2, 8.2); 0.98 (m, 1H); 0.57(m, 2H); 0.39 (m, 1H); 0.26 (m, 1H).

FAB (negative ion mode): M−1=129.

EXAMPLE 4

Preparation of cis-3-cyclopropylacrylic acid, trans-3-cyclopropylacrylic acid and vinylcyclopropane from poly(3-cyclopropyl-3-hydroxypropionate)

CPCA (292.5 g, 4.2 moles) was charged to a 0.5 L, 2-neck flask with a built in thermowell. Anhydrous zinc acetate dihydrate (2.66 g, 0.0035 moles) was added as a single charge and stirred although not all of the catalyst went into solution. Ketene was introduced through an extra coarse fritted gas inlet tube and allowed to exit the reaction vessel through a dry ice cooled condenser. Approximately 144 g of ketene (3.4 moles) was added over the course of 2.7 hours. After an initial warm-up period, the reaction temperature was maintained between 46 and 60° C. by application of an external cooling bath during the early phase of the reaction (approximately 1.5 hr) and with external heating during the latter phases of the reaction. Proton NMR analysis revealed approximately 33 mole percent of unreacted CPCA relative to polymer product. Metal analysis of the crude reaction product (409.9 g) showed 1730 ppm Zn. The majority of this product (356 g) was transferred to distillation vessel (1L) equipped with a thermowell. The remaining CPCA monomer was removed by vacuum treatment (1–10 Torr) and brief heating of the polymer (30 min) to 140° C. The polymeric product which remained (262.9 g, estimated to contain approximately 2.33 moles of polymer repeat units) was then heated at modest vacuum (310 to 420 Torr) up to a temperature of 250° C. over an approximate 40 minute period. The reaction temperature was then held at 250° C. for an additional 10 minutes. The gases produced from this reaction (<213° C.) were passed through a water cooled short path condenser of approximately 13 mm (0.5 inch) inside diameter and approximately 7.6 cm (3 inch) length into a ambient temperature receiver. The gasses which did not condense in the condenser or the ambient temperature receiver were passed through an approximate 30.5 cm (12 inch) length of vacuum tubing to a dry ice condenser and into a receiver.

Proton NMR analysis of the contents of the ambient temperature receiver (86.9 g, 0.77 moles, approximately 33% yield) indicate that the major components were cis-3-cyclopropylacrylic acid and trans-3-cyclo-propyl acrylic acid in a ratio of approximately 1:6. This mixture of cis-3-cyclopropylacrylic acid and trans-3-cyclopropylacrylic acid crystallized on standing. Filtration and isolation of the solids provided trans-3-cyclo-propylacrylic acid.

Proton NMR analysis of the contents of the dry ice receiver (40.3 g, 0.59 moles, approximately 25% yield) indicated the presence of vinyl-cyclopropane at a purity which was estimated at greater than 90 mole%. The material which remained in the reaction vessel (74.6 g) represented 28 weight percent of the initial polymer charge. Additional product could be obtained on further heating but was of low purity.

Vinylcyclopropane (the proton NMR matches a published spectrum for vinylcyclopropane which was prepared by a more indirect route, see J. E. Baldwin, K. A. Villarica, *J. Org. Chem.*, 1995, 60, 186.):

$^1$H NMR (CDCl$_3$): 5.35(ddd, 1H, J=17.1, 10.1, 8.7); 5.08(dd, 1H, J=17.1, 1.8); 4.85(dd, 1H, J=10.1, 1.8), 1.42(m, 1H), 0.72(m, 2H), 0.39(m, 2H).

GCMS/EIMS (m/e): M+1=69.

trans-3-cyclopropylacrylicacid:

$^1$H NMR (CDCl$_3$): 6.52(dd, 1H, J=15.4, 10.2); 5.90(d, 1H, J=15.4); 1.61(m, 1H); 1.00(m, 2H); 0.68(m, 2H).

GCMS(EIMS): M+1=113

EXAMPLE 5

Preparation of vinylcyclopropane from 3-cyclopropyl acrylic acid

A sample of trans-3-cyclopropylacrylic acid (cis- content less than 5%, 10.06 g, 0.090 mole) was charged to a 25 mL reaction vessel which was equipped with an internal thermowell. The contents of the reactor were brought to 230–240° C. and maintained at that temperature for approximately two hours. The reaction gasses which were produced were passed through a water cooled short path condenser (approximately 4 cm in length, 0.5 cm ID) and into a dry-ice (−78° C.) cooled receiver. The temperature at the inlet to the water cooled condenser never exceeded 30° C. After the reactor contents had been allowed to cool to room temperature, the contents of the dry-ice cooled receiver were weighed (1.67 g, 0.025 mole) and analyzed by proton NMR. NMR analysis of the contents of the receiver showed it to contain vinylcyclopropane in high purity (estimated at greater than 90 mole percent). No traces of 3-cyclopropylacrylic acid were detected in the receiver contents.

EXAMPLE 6

Preparation of methyl 3-cyclopropyl-3-hydroxypropionate Poly(3-cyclopropyl-3-hydroxypropionate) was prepared according to the procedure described in Example 2. The CPCA monomer present in the crude product was removed by vacuum treatment (1–7 torr) and brief heating of the polymer (20 minutes) to 100° C. The thus formed poly(3-cyclopropyl-3-hydroxypropionate) (15.6 g) was charged to a 250 mL flask with methanol (100 mL) and sulfuric acid (0.71 g). The reaction mixture was maintained at reflux for 3 hours and then left to stir for 5 days at room temperature. The resulting homogeneous solution was neutralized by passing it through a quaternary ammonium hydroxide anion exchange resin (Bio-Rad AG 1-X8, 50 mL, approximately 20–50 mesh, approximately 0.3–0.8 mm). The resultant solution was concentrated under vacuum and distilled through a short path distillation apparatus to provide methyl 3-cyclopropyl-3-hydroxypropionate (6.6 g, bp 74–75, 0.5 torr)

$^1$H NMR (CDCl$_3$): 3.72 (s, 3H); 3.33 (m, 1H); 2.64 (m, 2H); 2.56 (bs, OH, 1H); 0.95 (m, 1H); 0.54 (m, 2H); 0.43 (m, 1H); 0.24 (m, 1H).

GCMS/EIMS (mie): M+1=145.

EXAMPLE 7

Preparation of (1,2-dibromoethyl)cyclopropane from vinylcyclopropane

A redistilled sample of vinylcyclopropane (9.7 g, 0.14 mole), prepared as in Example 4, and n-heptane were charged to a 300 mL, two-neck, glass reaction vessel equipped with a built in thermowell. The reactor contents were cooled to 0° C. using a −20° C. ethanol cooling bath. Bromine (21.2 g, 0.13 mole) was slowly added via an addition funnel at a rate such that the reaction solution was maintained between −8 and 1° C. Distillation of the crude reaction mixture through a 12 inch vigereux separation column provided (1,2-dibromoethyl)cyclopropane (20.5 g, approximately 0.9 mole). A significant amount of (1,2-dibromoethyl)cyclopropane remained in the undistilled pot residue along with higher boiling materials.

$^1$H NMR (CDCl$_3$): 3.86(m, 2H); 3.64(m, 1H); 1.30(m, 1H); 0.95(m, 1H); 0.78(m, 1H); 0.67(m, 1H); 0.42(m, 1H).

GCMS/EIMS (m/e): M+=226,228,230 (very weak), (M−28)+=198,200,202

EXAMPLE 8

Preparation of cyclopropylacetylene from 1-cyclopropyl-1,2-dibromoethane

The (1,2-dibromoethyl)cyclopropane of Example 5 (4.56 g; 0.020 mole) was dissolved in 10 mL of DMSO. Crushed potassium hydroxide (4.21 g; 0.075 mole; 3.75 equiv.) was added in two portions and the reaction mixture heated for a total of 11 hours to consume the starting material and form cyclopropylacetylene. The reaction mixture was cooled to ambient temperature and water (10 mL) was added. The product was distilled in vacuo at ambient temperature and the volatiles were condensed at −78° C. to afford 0.56 g of cyclopropylacetylene which was 86% pure according to GC analysis (indicating a 36% yield).

$^1$ H NMR (CDCl$_3$): 1.752 (d, 1H, J=2.20 Hz); 1.23 (m, 1H); 0.77 (m, 2H); 0.72 (m, 2H).

GC (30 m DB–17, 50° C., 10 min, 50–100° C., 10/min, 100° C., 5 minutes): $t_R$ 3.61 minutes.

EXAMPLE 8

Preparation of 3-cyclpropylacrylic acid and 3-cyclopropyl-3-hydroxypro-pionic acid by caustic hydrolysis of poly(3-cyclopropyl-3-hydroxypropionate)

Poly(3-cyclopropyl-3-hydroxypropionate) was prepared according to the procedure described in Example 2. The polymer (260.5 g, approximately 2.18 moles of repeat units) was charged to a 2 L glass reactor which was equipped for mechanical stirring, with an internal thermowell and with a reflux condenser. Water (100 ml) was added and the two phase mixture was brought to reflux. External heating was discontinued and 50% aqueous caustic (279.48 g, approximately 3.5 moles) was added at a rate such that gentle reflux was maintained (approximately 15 minutes) The liquid, apparently homogenous reaction mixture was then brought to vigorous reflux and maintained at a temperature of approximately 108° C. for 2 hours. Heating of the reaction was discontinued and the reaction mixture was allowed to cool to approximately 80° C. whereupon addition of concentrated HCl was started. Gentle cooling of the reaction was applied with an external room temperature water cooling bath although an attempt was made to keep the temperature of the partially neutralized reaction mixture above 40° C. in order to permit stirring. Upon completion of the HCl addition (approximately 310 ml, approximately 3.7 moles) the pH was checked (approximately 1.5) using narrow range pH paper. The reaction mixture was cooled in a water-ice bath for approximately 1 hour and then filtered. The obtained solids were washed with a small portion of water (200 ml) and air dried overnight (approximately 148 g, approximately 1.3 moles, approximately 60%). The aqueous filtrate was extracted with two portions of ethyl acetate (2×250 ml). The organic phase was dried by filtration through magnesium and sodium sulfate and concentrated in vacuo (approximately 84 g, approximately 0.65 moles, approximately 30%). Proton NMR analysis of the filtered solids indicated the presence of 3-cyclopropyl-3-hydroxypropionic acid, trans-3-cyclopropylacrylic acid and cis-3-cyclopropylacrylic acid in a molar ratio of approximately 2:17:1. Proton NMR analysis of the concentrated filtrate indicated the presence of 3-cyclopropyl-3-hydroxypropionic acid, trans-3-cyclopropylacrylic acid and cis-3-cyclopropylacrylic acid in a molar ratio of approximately 17:2:1.

The invention has been described in detail with particular reference to preferred embodiments thereof, but it will be understood that variations and modifications can be effected within the spirit and scope of the invention.

We claim:

1. A composition having the formula

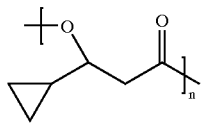

I wherein n is greater than 1.

2. The composition of claim 1 wherein n is about 10 to 100.

3. Process for the preparation of a composition having the formula

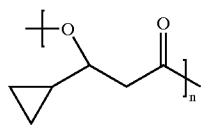

I wherein n is greater than 1 which comprises reacting cyclopropane-carboxaldehyde and ketene in the presence of a catalyst selected from Lewis acids and tertiary amines.

4. Process according to claim 3 wherein n is about 10 to 100 and cyclopropanecarboxaldehyde and ketene are reacted at a temperature of about 0 to 100° C. in the presence of a catalyst wherein the catalyst is an iron carboxylate, a zinc carboxylate, a magnesium carboxylate or boron trifluoride.

5. Process according to claim 4 wherein cyclopropanecarboxaldehyde and ketene are reacted at a temperature of about 40 to 70° C. in the presence of a catalytic amount of a zinc carboxylate.

6. Process according to claim 5 wherein the zinc carboxylate is zinc acetate or zinc 2-ethylhexanoate.

7. A mixed carboxylic anhydride comprising a 3-cyclopropyl-3-acyloxy-propionyl residue and the acyl residue of a $C_2$–$C_{14}$ carboxylic acid wherein the acyloxy group is the residue of the $C_2$–$C_{14}$ carboxylic acid.

8. A mixed carboxylic anhydride according to claim 7 comprising 3-cyclopropyl-3-acetoxypropionyl residue and an acetyl residue.

* * * * *